(12) United States Patent
Bareket et al.

(10) Patent No.: US 7,515,253 B2
(45) Date of Patent: Apr. 7, 2009

(54) SYSTEM FOR MEASURING A SAMPLE WITH A LAYER CONTAINING A PERIODIC DIFFRACTING STRUCTURE

(75) Inventors: Noah Bareket, Saratoga, CA (US);
Daniel C. Wack, Los Altos, CA (US);
Guoheng Zhao, Milpitas, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 368 days.

(21) Appl. No.: 11/329,500

(22) Filed: Jan. 10, 2006

(65) Prior Publication Data

US 2008/0037005 A1     Feb. 14, 2008

Related U.S. Application Data

(60) Provisional application No. 60/643,711, filed on Jan. 12, 2005.

(51) Int. Cl.
*G01B 11/02*     (2006.01)
(52) U.S. Cl. .................. 356/73; 356/369; 356/625; 356/636
(58) Field of Classification Search ......... 356/503–504, 356/630, 632, 908
See application file for complete search history.

(56) References Cited

U.S. PATENT DOCUMENTS

| | | | |
|---|---|---|---|
| 3,426,201 A | 2/1969 | Hilton et al. | |
| 3,547,074 A | 12/1970 | Hirschfeld | |
| 3,667,846 A | 6/1972 | Nater et al. | |
| 3,671,126 A | 6/1972 | Erb | |
| 4,039,370 A | 8/1977 | Kleinknecht | |
| 4,141,780 A | 2/1979 | Kleinknecht et al. | |
| 4,146,327 A | 3/1979 | Harris | |
| 4,149,089 A | 4/1979 | Idelsohn et al. | |
| 4,168,437 A | 9/1979 | Nihonmatsu | |
| 4,171,917 A | 10/1979 | Pirlet | |
| 4,173,788 A | 11/1979 | Laliotis | |
| 4,200,396 A | 4/1980 | Kleinknecht et al. | |

(Continued)

FOREIGN PATENT DOCUMENTS

DE     41 05 192 A1     8/1991

(Continued)

OTHER PUBLICATIONS

Arimoto, H., "Precise Line-and-Space Monitoring Results by Ellipsometry", *Jpn. J. Appl. Phys.* vol. 36, Part 2, No. 2A, Feb. 1997, pp. L173-L175.

(Continued)

*Primary Examiner*—F. L Evans
(74) *Attorney, Agent, or Firm*—Davis Wright Tremaine LLP (57) ABSTRACT

To measure the critical dimensions and other parameters of a one- or two-dimensional diffracting structure of a film, the calculation may be simplified by first performing a measurement of the thickness of the film, employing a film model that does not vary the critical dimension or parameters related to other characteristics of the structure. The thickness of the film may be estimated using the film model sufficiently accurately so that such estimate may be employed to simplify the structure model for deriving the critical dimension and other parameters related to the two-dimensional diffracting structure.

35 Claims, 10 Drawing Sheets

U.S. PATENT DOCUMENTS

| | | | |
|---|---|---|---|
| 4,303,341 A | 12/1981 | Kleinknecht et al. | |
| 4,330,213 A | 5/1982 | Kleinknecht et al. | |
| 4,373,804 A | 2/1983 | Pryor et al. | |
| 4,408,884 A | 10/1983 | Kleinknecht et al. | |
| 4,516,855 A | 5/1985 | Korth | |
| 4,615,620 A * | 10/1986 | Noguchi et al. | 356/626 |
| 4,634,232 A | 1/1987 | Tateoka | |
| 4,650,335 A | 3/1987 | Ito et al. | |
| 4,653,924 A | 3/1987 | Itonaga et al. | |
| 4,655,595 A | 4/1987 | Bjork et al. | |
| 4,668,860 A | 5/1987 | Anthon | |
| 4,672,196 A | 6/1987 | Canino | |
| 4,687,325 A | 8/1987 | Corby, Jr. | |
| 4,689,491 A | 8/1987 | Lindow et al. | |
| 4,695,162 A | 9/1987 | Itonaga et al. | |
| 4,710,642 A | 12/1987 | McNeil | |
| 4,790,659 A | 12/1988 | Erman et al. | |
| 4,905,170 A | 2/1990 | Forouhi et al. | |
| 4,964,726 A | 10/1990 | Kleinknecht et al. | |
| RE33,424 E * | 11/1990 | Noguchi et al. | 356/626 |
| 4,991,971 A | 2/1991 | Geary et al. | |
| 4,999,014 A | 3/1991 | Gold et al. | |
| 5,018,863 A | 5/1991 | Vareille et al. | |
| 5,032,734 A | 7/1991 | Orazio, Jr. et al. | |
| 5,042,951 A | 8/1991 | Gold et al. | |
| 5,076,696 A | 12/1991 | Cohn et al. | |
| 5,091,320 A | 2/1992 | Aspnes et al. | |
| 5,125,040 A | 6/1992 | Matsui et al. | |
| 5,164,579 A | 11/1992 | Pryor et al. | |
| 5,164,790 A | 11/1992 | McNeil et al. | |
| 5,166,752 A | 11/1992 | Spanier et al. | |
| 5,170,049 A | 12/1992 | De Jonge et al. | |
| 5,173,719 A | 12/1992 | Taniguchi et al. | |
| 5,241,369 A | 8/1993 | McNeil et al. | |
| 5,270,794 A | 12/1993 | Tsuji et al. | |
| 5,280,179 A | 1/1994 | Pryor et al. | |
| 5,313,044 A | 5/1994 | Massoud et al. | |
| 5,329,357 A | 7/1994 | Bernoux et al. | |
| 5,333,052 A | 7/1994 | Finarov | |
| 5,337,146 A | 8/1994 | Azzam | |
| 5,337,150 A | 8/1994 | Mumola | |
| 5,355,212 A | 10/1994 | Wells et al. | |
| 5,361,137 A | 11/1994 | Aton et al. | |
| 5,362,970 A | 11/1994 | Pryor et al. | |
| 5,365,340 A | 11/1994 | Ledger | |
| 5,381,233 A | 1/1995 | Chao et al. | |
| 5,386,317 A | 1/1995 | Corle et al. | |
| 5,393,624 A | 2/1995 | Ushijima | |
| 5,399,229 A | 3/1995 | Stefani et al. | |
| 5,408,322 A | 4/1995 | Hsu et al. | |
| 5,412,473 A | 5/1995 | Rosencwaig et al. | |
| 5,416,594 A | 5/1995 | Gross et al. | |
| 5,420,680 A | 5/1995 | Isobe et al. | |
| 5,432,607 A | 7/1995 | Taubenblatt | |
| 5,438,415 A | 8/1995 | Kazama et al. | |
| 5,450,201 A | 9/1995 | Katzir et al. | |
| 5,486,919 A | 1/1996 | Tsuji et al. | |
| 5,494,697 A | 2/1996 | Blayo et al. | |
| 5,503,707 A | 4/1996 | Maung et al. | |
| 5,504,582 A | 4/1996 | Johs et al. | |
| 5,510,625 A | 4/1996 | Pryor et al. | |
| 5,517,312 A | 5/1996 | Finarov | |
| 5,519,793 A | 5/1996 | Grannes | |
| 5,521,706 A | 5/1996 | Green et al. | |
| 5,526,117 A | 6/1996 | Wielsch et al. | |
| 5,596,411 A | 1/1997 | Fanton et al. | |
| 5,604,581 A | 2/1997 | Liu et al. | |
| 5,607,800 A | 3/1997 | Ziger | |
| 5,608,526 A | 3/1997 | Piwonka-Corle et al. | |
| 5,610,392 A | 3/1997 | Nagayama et al. | |
| 5,625,453 A | 4/1997 | Matsumoto et al. | |
| 5,625,455 A | 4/1997 | Nash et al. | |
| 5,631,171 A | 5/1997 | Sandstrom et al. | |
| 5,638,178 A | 6/1997 | Lacey et al. | |
| 5,654,903 A | 8/1997 | Reitman et al. | |
| 5,666,199 A | 9/1997 | Hess et al. | |
| 5,666,200 A | 9/1997 | Drevillon et al. | |
| 5,666,201 A | 9/1997 | Johs et al. | |
| 5,670,787 A | 9/1997 | Pryor et al. | |
| 5,674,652 A | 10/1997 | Bishop et al. | |
| 5,677,541 A | 10/1997 | Pryor et al. | |
| 5,691,545 A | 11/1997 | Pryor et al. | |
| 5,693,953 A | 12/1997 | Pryor et al. | |
| 5,703,692 A | 12/1997 | McNeil et al. | |
| 5,734,172 A | 3/1998 | Pryor et al. | |
| 5,739,909 A | 4/1998 | Blayo et al. | |
| 5,747,813 A | 5/1998 | Norton et al. | |
| 5,754,296 A | 5/1998 | Law | |
| 5,757,671 A | 5/1998 | Drevillon et al. | |
| 5,767,525 A | 6/1998 | Pryor et al. | |
| 5,773,840 A | 6/1998 | Pryor et al. | |
| 5,777,744 A | 7/1998 | Yoshii et al. | |
| 5,786,602 A | 7/1998 | Pryor et al. | |
| 5,805,290 A | 9/1998 | Ausschnitt et al. | |
| 5,811,825 A | 9/1998 | Pryor et al. | |
| 5,811,827 A | 9/1998 | Pryor et al. | |
| 5,825,498 A | 10/1998 | Thakur et al. | |
| 5,835,220 A | 11/1998 | Kazama et al. | |
| 5,835,221 A | 11/1998 | Lee et al. | |
| 5,854,491 A | 12/1998 | Pryor et al. | |
| 5,866,915 A | 2/1999 | Pryor et al. | |
| 5,866,916 A | 2/1999 | Pryor et al. | |
| 5,867,276 A | 2/1999 | McNeil et al. | |
| 5,877,491 A | 3/1999 | Pryor et al. | |
| 5,880,459 A | 3/1999 | Pryor et al. | |
| 5,880,838 A | 3/1999 | Marx | |
| 5,883,390 A | 3/1999 | Pryor et al. | |
| 5,923,423 A | 7/1999 | Sawatari et al. | |
| 5,956,148 A | 9/1999 | Celii | |
| 5,963,329 A | 10/1999 | Conrad et al. | |
| 5,981,965 A | 11/1999 | Pryor et al. | |
| 5,982,496 A * | 11/1999 | Ziger | 356/630 |
| 6,031,615 A | 2/2000 | Meeks et al. | |
| 6,100,985 A * | 8/2000 | Scheiner et al. | 356/630 |
| 6,104,486 A | 8/2000 | Arimoto | |
| 6,118,525 A | 9/2000 | Fossey et al. | |
| 6,127,689 A | 10/2000 | Pryor et al. | |
| 6,138,055 A | 10/2000 | Pryor | |
| 6,157,451 A | 12/2000 | Mizuno | |
| 6,211,506 B1 | 4/2001 | Pryor et al. | |
| 6,263,099 B1 | 7/2001 | Maeda et al. | |
| 6,271,047 B1 | 8/2001 | Ushio et al. | |
| 6,278,519 B1 | 8/2001 | Rosencwaig et al. | |
| 6,323,946 B1 | 11/2001 | Norton | |
| 6,476,920 B1 * | 11/2002 | Scheiner et al. | 356/630 |
| 6,483,580 B1 | 11/2002 | Xu et al. | |
| 6,590,656 B2 | 7/2003 | Xu et al. | |
| 6,594,012 B2 | 7/2003 | Takeuchi et al. | |
| 6,603,542 B1 | 8/2003 | Chase et al. | |
| 6,614,540 B1 | 9/2003 | Stirton | |
| 6,657,736 B1 | 12/2003 | Finarov et al. | |
| 6,678,043 B1 | 1/2004 | Vurens et al. | |
| 6,728,663 B2 | 4/2004 | Krukar et al. | |
| 6,829,057 B2 | 12/2004 | Opsal et al. | |
| 6,836,324 B2 * | 12/2004 | Scheiner et al. | 356/319 |
| 6,900,892 B2 * | 5/2005 | Shchegrov et al. | 356/369 |
| 6,982,792 B1 | 1/2006 | Woollam et al. | |
| 7,003,149 B2 | 2/2006 | Benesch et al. | |
| 7,099,005 B1 | 8/2006 | Fabrikant et al. | |
| 7,123,366 B2 * | 10/2006 | Scheiner et al. | 356/625 |
| 7,173,699 B2 | 2/2007 | Xu et al. | |
| 7,187,456 B2 * | 3/2007 | Scheiner et al. | 356/630 |
| 7,242,477 B2 * | 7/2007 | Mieher et al. | 356/401 |
| 7,280,212 B2 * | 10/2007 | Mieher et al. | 356/401 |

| | | | |
|---|---|---|---|
| 7,280,230 B2* | 10/2007 | Shchegrov et al. | 356/630 |
| 7,289,213 B2* | 10/2007 | Mieher et al. | 356/401 |
| 7,298,481 B2* | 11/2007 | Mieher et al. | 356/401 |
| 7,301,634 B2* | 11/2007 | Mieher et al. | 356/401 |
| 7,372,579 B2* | 5/2008 | Chen et al. | 356/504 |
| 2002/0113966 A1 | 8/2002 | Shchegrov et al. | |

FOREIGN PATENT DOCUMENTS

| | | |
|---|---|---|
| DE | 41 08 329 A1 | 9/1992 |
| EP | 0 061 237 B1 | 4/1986 |
| EP | 0 021 205 A1 | 12/1986 |
| EP | 0 300 508 A2 | 1/1989 |
| EP | 0 403 769 A2 | 12/1990 |
| EP | 0 458 418 A2 | 11/1991 |
| EP | 0480620 A2 | 4/1992 |
| EP | 0480620 A3 | 9/1992 |
| EP | 0 660 077 A2 | 6/1995 |
| EP | 1124163 A2 | 8/2001 |
| EP | 1073876 B1 | 12/2004 |
| EP | 1508772 A1 | 2/2005 |
| EP | 1124163 A3 | 7/2005 |
| FR | 2 597 976 A1 | 10/1987 |
| FR | 2 731 074 A1 | 8/1996 |
| JP | 54092286 A | 7/1979 |
| JP | 57187604 A | 11/1982 |
| JP | 58206120 A | 12/1983 |
| JP | 59-140420 | 8/1984 |
| JP | 60033003 A | 2/1985 |
| JP | 60074528 A | 4/1985 |
| JP | 60086843 A | 5/1985 |
| JP | 60128602 A | 7/1985 |
| JP | 60166808 A | 8/1985 |
| JP | 60236005 A | 11/1985 |
| JP | 61004905 A | 1/1986 |
| JP | 61004906 A | 1/1986 |
| JP | 61039852 A | 2/1986 |
| JP | 62150251 A | 7/1987 |
| JP | 63308507 A | 12/1988 |
| JP | 1026102 A | 1/1989 |
| JP | 1182707 A | 7/1989 |
| JP | 01-211937 | 8/1989 |
| JP | 01-285806 | 11/1989 |
| JP | 02-012002 | 1/1990 |
| JP | 03075504 A | 3/1991 |
| JP | 04042945 A | 2/1992 |
| JP | 04-176143 | 6/1992 |
| JP | 05-023620 | 4/1993 |
| JP | 06-147987 | 5/1994 |
| JP | 07-022483 | 1/1995 |
| JP | 07-074088 | 3/1995 |
| JP | 07-231023 | 8/1995 |
| JP | 07-270144 | 10/1995 |
| JP | H08-255751 A | 10/1996 |
| JP | H08-261727 A | 10/1996 |
| JP | H09-237812 A | 9/1997 |
| JP | 11119213 | 4/1999 |
| SU | 1146549 A | 3/1985 |
| SU | 1226042 A | 4/1986 |
| SU | 1695145 A1 | 11/1991 |
| WO | WO 99/45340 | 9/1999 |
| WO | WO 00/35002 | 6/2000 |
| WO | WO 03/054475 | 7/2003 |
| WO | WO2006/076484 | 7/2006 |

OTHER PUBLICATIONS

Bernoux et al., "Ellipsometrie," Techniques de l'Ingenieur, 1990, R6490, pp. 1-16, (28 pages of translation included).

Blayo et al., "Ultraviolet-visible Ellipsometry for Process Control During the Etching of Submicrometer Features", *J. Opt. Soc. Am. A.*, vol. 12, No. 3, Mar. 1995, pp. 591-599.

Corle, T.R., "A broadband UV small spot spectroscopic ellipsometer," *SPIE Microlithography*, 1995, pp. 1-12.

Coulombe et al., "Ellipsometric-Scatterometry for sub-0.1 μm CD Measurements", Center for High Technology Materials, University of New Mexico, Spie, vol. 3332, pp. 283-292.

Diffraction: www.scienceworld.wolfram.com/physics/Diffraction.html, 2 pages, printed Jan. 27, 2004.

Forouhi, A.R. et al., "Optical dispersion relations for amorphous semiconductors and amorphous dielectrics," *Physical Review B*, vol. 34, No. 10, Nov. 15, 1986, pp. 7018-7026.

Forouhi, A.R. et al., "Optical properties of crystalline semiconductors and dielectrics," *Physical Review B*, vol. 38, No. 3, Jul. 15, 1988, pp. 1865-1873.

Gaylord, T.K. et al., "Analysis and Applications of Optical Diffraction by Gratings," *Proceedings of the IEEE*, vol. 73, No. 5, May 1985, pp. 894-937.

Haggans et al., "Effective-Medium Theory of Zeroth-Order Lamellar Gratings in Conical Mountings," J. Opt. Soc. Am. A, Oct. 19, 1993, vol. 10, No. 10, pp. 2217-2225.

Ibok, E. et al., "Optical characterization of amorphous and polycrystalline silicon films," *Solid State Technology*, Aug. 1995, 4 pages.

Kikuta et al., "Effective Medium Theory of Two-Dimensional Subwavelength Gratings in the Non-Quasi-Static Limit," J. Opt. Soc. Am. A, vol. 15, No. 6, Jun. 1998, pp. 1577-1585.

Lalanne et al., "High-Order Effective-Medium Theory of Subwavelength Gratings in Classical Mounting: Application to Volume Holograms," J. Opt. Soc. Am. A, vol. 15, No. 7, Jul. 1998, pp. 1843-1851.

Lalanne et al., "On the Effective Medium Theory of Subwavelength Periodic Structures," Journal of Modern Optics, 1996, vol. 43, No. 10, pp. 2063-2085.

Li, L., "A modal analysis of lamellar diffraction gratings in conical mountings," *Journal of Modern Optics*, vol. 40, No. 4, 1993, pp. 553-573.

Li L. et al., "Convergence of the coupled-wave method for metallic lamellar diffraction gratings," *Journal of the Optical Society of America A*, vol. 10, No. 6, Jun. 1993, pp. 1184-1188.

Li, L., "Formulation and Comparison of Two Recursive Matrix Algorithms for Modeling Layered Diffraction Gratings," J. Opt. Soc. Am. A, vol. 13, No. 5, May 1996, pp. 1024-1035.

Li L., "Multilayer modal method for diffraction gratings of arbitrary profile, depth, and permittivity," *Journal of the Optical Society of America A*, vol. 10, No. 12, Dec. 1993, pp. 2581-2591.

McNeil, J.R. et al., "Scatterometry Applied to Microelectronics Processing—Part 1", *Solid State Technology*, Mar. 1993, 3 pages.

McNeil, J.R. et al., "Scatterometry Applied to Microelectronics Processing—Part 2", *Solid State Technology*, Apr. 1993, pp. 53-56.

Mills., D. W. et al., "Spectral ellipsometry on patterned wafers", *SPIE's Microelectronic Manufacturing: Process, Equipment, and Materials Control in Integrated Circuit Manufacturing*, SPIE vol. 2637, Austin (USA). 1995. 12 pages.

Moharam, M.G., "Coupled-Wave Analysis of Two-Dimensional Dielectric Gratings," *Proc. SPIE*, vol. 883, Holographics Optics: Design and Applications, 1988, pp. 8-11.

Moharam, M.G. et al., "Formulation for Stable and Efficient Implementation of the Rigorous Coupled-Wave Analysis of Binary Gratings," *J. Opt. Soc. Am. A*, vol. 12, May 1995, pp. 1068-1076.

Moharam, M.G. et al., "Rigorous coupled-wave analysis of planar-grating diffraction," *J. Opt. Soc. Am.*, vol. 71, No. 7, Jul. 1981, pp. 811-818.

Moharam, M.G. et al., "Stable implementation of the rigorous coupled-wave analysis for surface-relief gratings: enhanced transmittance matrix approach," *J. Opt. Soc. Am. A.*, vol. 12, No. 5, May 1995, pp. 1077-1086.

Murnane et al., "Developed Photoresist Metrology Using Scatterometry", Center for High Technology Materials, University of New Mexico, *SPIE*, vol. 2196, pp. 47-59.

Pforr, R. et al., "In-Process Image Detecting Technique For Determination Of Overlay, And Image Quality For ASM-L Wafer Stepper", *SPIE* vol. 1674 *Optical/Laser Microlithography V*, 1992, pp. 594-608.

Physics 2049C Laboratory 13 Diffraction Grating, www.physics.fsu.edu/courses/fall98/phy2049c/labs/L13.pdf, 7 pages.

Raymond, C.J. et al., "Metrology of subwavelength photoresist gratings using optical scatterometry," *J. Vac. Sci. Technol. B*, vol. 13, No. 4, Jul./Aug. 1995, pp. 1484-1495.

Sohail, S. et al., "Scatterometry and the Simulation of the Diffraction-Based Metrology", *Micro-lithography World*, Jul./Aug./Sep. 1993, pp. 5-16.

"Spectroscopic Ellipsometry—A Technology Primer", KLA-Tencor, 12 pages.

Tompkins et al., "Spectroscopic Ellipsometry and Reflectometry: A User's Guide," John Wiley & Sons, Inc., New York, 1999, 9 pages.

Wang et al., "Influence of semiconductor manufacturing process variation on device parameter measurement for angular scatterometry," SPIE Microlithograohy World 2006, 9 pages.

Ziger, D.H. et al., "Line size effects on ultraviolet reflectance spectra," *Opt. Eng.*, vol. 36, No. 1, Jan. 1997, pp. 243-250.

Azzam et al., "Polarization Characteristics of Scattered Radiation from a Diffraction Grating by Ellipsometry with Application to Surface Roughness," Physical Review B, vol. 5, No. 12, Jun. 15, 1972, pp. 4721-4729.

Baker, "Polarization Micro-Metrology", SPIE, vol. 1166 Polarization Considerations for Optical Systems II, 1989, pp. 188-197.

Bishop et al., "Grating line shape characterization using scatterometry," SPIE, vol. 1545, International Conference on the Application and Theory of Periodic Structures, 1991, pp. 64-73.

Brundle et al. (Series editors), "Encyclopedia of Materials Characterization," Materials Characterization Series. Surfaces, Interfaces, Thin Films. Copyrights 1992 by Butterworth-Heinemann. Whole book.

Butler et al., "Supervisory Run-to-Run Control of Polysilicon Gate Etch Using In Situ Ellipsometry," IEEE Transactions on Semiconductor Manufacturing, vol. 7, No. 2, May 1994, pp. 193-201.

Hatab et al., "Sixteen-megabit dynamic random access memory trench depth characterizing using two-dimensional diffraction analysis," J. Vac. Sci. Technol. B 13(2), Mar./Apr. 1995, pp. 174-182.

Haverlag et al., "In situ ellipsometry and reflectometry during etching of patterned surfaces: Experiments and simulations," J. Vac. Sci. Technol. B 10(6), Nov./Dec. 1992, pp. 2412-2418.

Heissmeier, "Calibration of a microlithographic fabrication process using non-destructive testing and rigorous electromagnetic theory," OPTIK, vol. 103, Issue 1, pp. 12-18. Published in Jul. 1996.

Hickman et al., "Use of Diffracted Light from Latent Images to Improve Lithography Control", J. Vac. Sci. Technol. B 10, No. 5, Sep./Oct. 1992, pp. 2259-2266.

Irene, "Applications of spectroscopic ellipsometry to microelectronics," Thin Solid Films, 233 (1993), pp. 96-111.

Jacobson et al., "Comparison of Optical Scatterometer and Profilometer Techniques for Characterizing Smooth Surfaces," SPIE vol. 1009, Surface Measurement and Characterization, 1988, pp. 77-80.

Jacobson et al., "Microstructure characterization by angle-resolved scatter and comparison to measurements made by other techniques," Applied Optics, vol. 31, No. 10, Apr. 1, 1992, pp. 1426-1435.

Krukar, "A Methodology for the Use of Diffrated Scatter Analysis to Measure the Critical Dimensions of Periodic Structures", Dissertation, The University of New Mexico, May 1993, pp. 1-66.

Krukar et al., "Wafer examination and critical dimension estimation using scattered light," SPIE vol. 1661 (1992), pp. 323-332.

Milner et al., "Stepper focus characterization using diffraction from latent images," J. Vac. Sci. Technol. B 11(4), Jul./Aug. 1993, pp. 1258-1266.

Minhas et al., "Ellipsometry scatterometry for the metrology of sub-0.1-μm-linewidth structures," Applied Optics, vol. 37, No. 22, Aug. 1, 1998, pp. 5112-5115.

Moharam et al., "Three-dimensional vector coupled-wave analysis of planar-grating diffraction," J. Opt. Soc. Am., vol. 73, No. 9, Sep. 1983, pp. 1105-1112.

Naqvi et al., "Etch depth estimation of large-period silicon gratings with multivariate calibration of rigorously simulated diffraction profiles," J. Opt. Soc. Am. A, vol. 11, No. 9, Sep. 1994, pp. 2485-2493.

Pai et al., "Analysis of dielectric gratings of arbitrary profiles and thicknesses," J. Opt. Soc. Am. A, vol. 8, No. 5, May 1991, pp. 755-762.

Peng et al., "Analysis of Periodic Thin-Film Structures with Rectangular Profiles," Optics Communications, vol. 10, No. 1, Jan. 1974, pp. 91-94.

Qu et al., "Polarization dependence of the electromagnetic field distribution across wavelength-sized relief grating surfaces," J. Opt. Soc. Am. A, vol. 10, No. 11, Nov. 1993, pp. 2317-2323.

Raymond et al., "Multiparameter grating metrology using optical scatterometry," J. Vac. Sci. Technol. B 15(2), Mar./Apr. 1997, pp. 361-368.

Smet et al., "Ellipsometry of anisotropic substrates: Re-examination of a special case," J. Appl. Phys. 76 (5), Sep. 1, 1994, pp. 2571-2574.

Sohail et al., "A Simple Technique for Linewidth Measurement of Gratings on Photomasks," SPIE vol. 1261, Integrated Circuit Metrology, Inspection, and Process Control IV (1990), pp. 495-504.

Sohail et al., "Grating Parameter Estimation using Scatterometry," SPIE vol. 1992 Miniature and Micro-Optics and Micromechanics (1993), pp. 170-180.

Stover, "Optical Scattering—Measurement and Analysis", Copyrights 1995 by The Society of Photo-Optical Instrumentation Engineers. Whole book.

EP0/ISR, "PCT International Search Report and the Written Opinion," International Application PCT/US06/01067, Jul. 3, 2008, 10 pages.

Japanese Patent Office, "First Office Action," corresponding Japanese Patent Application No. 2003-555142 on Sep. 22, 2008, 7 pages.

Japanese Patent Office, "First Office Action," corresponding Japanese Patent Application No. 2000-534831 on Sep. 26, 2008, 8 pages.

* cited by examiner

Film Pad with Floating n&k, t = 3967A

NGOF = 0.9907    $X^2$ = 129.9

NGOF = 0.7684    Grating with Film n&k Float Thickness only, t = 3932.67A    X² = 7235.4

FIG. 7

FIG. 8

SYSTEM FOR MEASURING A SAMPLE WITH A LAYER CONTAINING A PERIODIC DIFFRACTING STRUCTURE

CROSS-REFERENCE TO RELATED APPLICATION

This application claims the benefit of U.S. Provisional Application No. 60/643,711, filed Jan. 12, 2005, entitled "System for Measuring a Sample with a Layer Containing a Periodic Diffracting Structure," which application is incorporated in its entirety by reference as if fully set forth herein.

BACKGROUND OF THE INVENTION

This invention relates, in general, to optical sample measurement systems, and in particular, to a system for measuring a sample with a layer containing a periodic diffracting structure.

In semiconductor wafer processing, or similar applications, one frequently encounters the measurements of the dimensions and/or profiles of structures etched in thin films, such as contact holes etched in a resist film or in a dielectric layer. The conventional method for measuring the dimensions and/or profiles of the structures is by means of a spectroscopic scatterometry or spectroscopic critical dimension measurements (SCD). In the current SCD method, the spectrum of specular reflectance of a wide band light beam is used to measure parameters, such as height, width or diameter (also known as critical dimension), and wall angle of an array of contact holes or lines etched in the film. To perform the measurements, the reflectance spectra are calculated using a model of the structure, as a function of the model parameters. An algorithm is then used to find the best values of the model parameters that fit the spectra. If there are multiple model parameters that need to be accounted for in the model of the structure, the calculation of the spectra is time-consuming, and becomes impractical to complete in real time (such as in a few seconds).

To avoid this problem, in a variant of the current method, a neighboring area of the film or layer on the wafer not containing the structures is measured independently to obtain the thickness information. Assuming that the film or layer of the neighboring area and the film or layer with the structures of interest (e.g. contact holes) have the same film index and thickness characteristics, such thickness value may be subsequently used in the construction of the structure model, thereby reducing the number of model parameters. This results in reducing modeling complexity and calculation time.

The above-described conventional methods are disadvantageous for a number of reasons. First, simplifying the modeling by first performing independent and separate measurements of a neighboring area may not always be possible, since such neighboring areas may not be always available. Even if such area is available, the film thickness in such area may be substantially different from the thickness or height of the etched film structure of interest. If no separate measurements are performed on a neighboring area, and as noted, the calculation may take too much time for applications where the calculations must be preformed in real time. It is therefore desirable to provide an improved system whereby the above-described shortcomings are overcome.

SUMMARY OF THE INVENTION

This invention is based on the recognition that, to simplify the construction of structure models, film thickness information on the same area of the wafer that contains the target diffracting structures may be obtained to facilitate the derivation of parameters pertaining to the diffracting structures using a structure model of the target structures. The value of the film thickness may then be used in the construction or application of the structure model of the target structure to reduce the number of model parameters and to simplify the calculation of the signal spectra. In one embodiment, the film thickness may be obtained from the same diffraction data that is used to derive the parameters pertaining to the diffracting structures, so that a single measurement suffices in obtaining data sufficient for the process where the film thickness is first obtained from the data, and then the parameters pertaining to the diffracting structures are derived from the same data. In an alternative embodiment, film thickness measurements on the same area of the wafer that contains the target diffracting structures may be first performed, and the film thickness may be found using a film model. Then, a separate measurement on the diffracting structures is performed to obtain data from which parameters pertaining to the diffracting structures are derived.

Preferably, the film model used in the process for obtaining film thickness does not vary or parameterize any quantity related to the diffracting structure, such as pitch, critical dimension, side wall angle or other profile related parameters. Preferably, the diffracting structure is illuminated by means of radiation of a plurality of wavelengths (e.g. wavelengths in the range of 230 to 850 nanometers). The diffraction of the beam is detected preferably at a plurality of wavelengths and one or more parameters related to the diffracting structure is then determined using the thickness value found and the diffraction detected. The above described system is particularly useful for measuring certain types of structures in the film, using radiation detected within certain regions in the signal spectra. The diffraction may be detected using any suitable instrument, such as a spectroscopic scatterometer, reflectometer, ellipsometer or polarimeter.

BRIEF DESCRIPTION OF THE DRAWINGS

FIGS. 4A, 4B, 4C, and 4D are graphical plots showing a comparison of the measured values and those predicted by a model of ellipsometric parameters $\alpha$, $\beta$ and the reflectivities of the S-polarization and P-polarization components, respectively, of radiation scattered by a film pad without holes therein, used for illustrating the invention. In FIGS. 4A-4D, the model is one where the complex index of refraction n and k are varied to yield a value of film thickness of 3967 A.

FIGS. 5A, 5B, 5C, and 5D are graphical plots showing a comparison of the measured values and those predicted by a model of the ellipsometric parameters α, β and of the S-polarization and P-polarization components, respectively, of radiation scattered by a film pad with a two-dimensional array of holes therein measured using the apparatus of FIG. 2. In FIGS. 5A-5D, the model is one where the complex index of refraction n and k as well as thickness are varied to yield a value of film thickness of 3970.08 A.

FIGS. 6A, 6B, 6C, and 6D are graphical plots showing a comparison of the measured values and those predicted by a model of the ellipsometric parameters α, β and of the S-polarization and P-polarization components, respectively, of radiation scattered by a film pad with a two-dimensional array of holes therein measured using the apparatus of FIG. 2. In FIGS. 5A-5D, the model is one where the thickness (but not the complex index of refraction n and k) is varied to yield a value of film thickness of 3932.67 A.

For simplicity in description, identical components are identified by the same numerals in this application.

DETAILED DESCRIPTION OF THE INVENTION

Figure 1A:
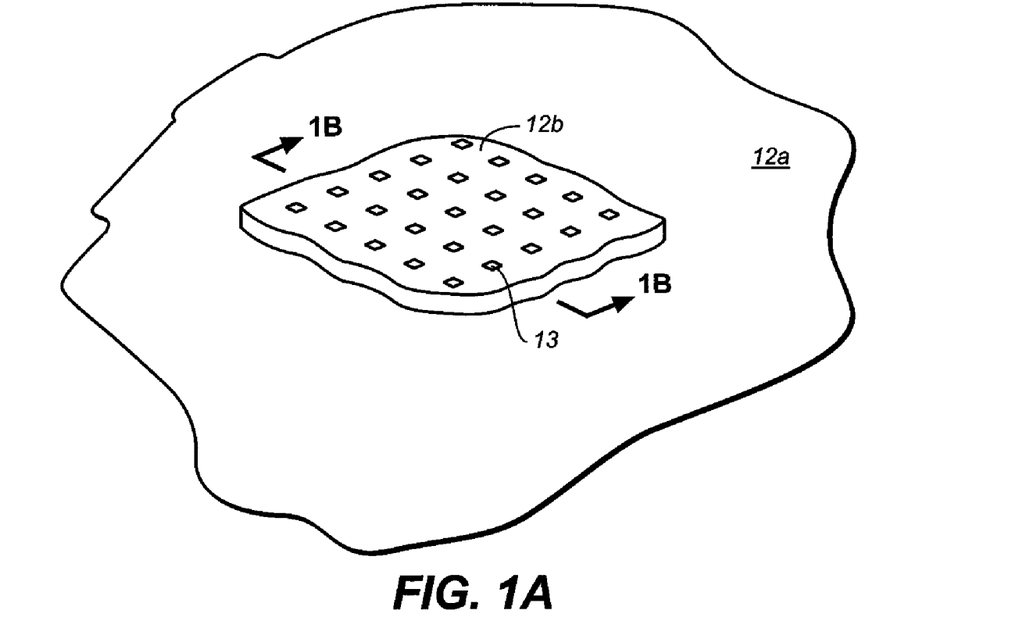
FIG. 1A is a perspective view of a portion of a semiconductor wafer having a layer with a two-dimensional array of contact holes therein, useful for illustrating the invention.
Figure 1B:
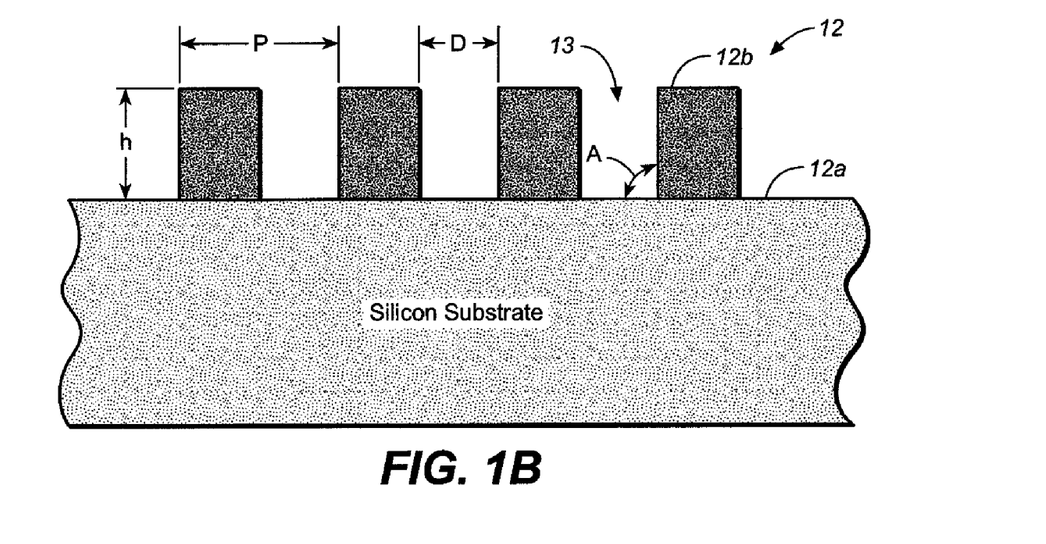
FIG. 1B is a cross-section view of a portion of the wafer and layer of FIG. 1A along the line 1B-1B in FIG. 1A.

FIG. 1A is a perspective view of a portion of a semiconductor wafer 12, having a silicon substrate 12a with a layer 12b thereon having a two-dimensional array of contact holes 13 therein. FIG. 1B is a cross-sectional view of wafer 12 of FIG. 1A along the line 1B-1B in FIG. 1A. The cross-sectional view of FIG. 1B is not drawn to the same scale as that in FIG. 1A. Each of the holes 13 in the array of contact holes has a diameter D and the holes are spaced apart at a pitch P, as shown in FIG. 1B. The layer 12b has a thickness or height of h and the side walls of the contact holes 13 are at an angle A to the top surface of the silicon substrate 12a.

In the conventional method, in order to be able to determine quantities such as D (the diameter of the holes 13), the pitch P, height or thickness, h, and the wall angle A, or other parameters related to the profile or shape of the contact holes 13, all of the above-referenced parameters, as well as the complex index of refraction of layer 12b are included in a model of the structure and regression is then used to find the best model parameters that fit the spectra. Calculation of the spectra involving such a large number of parameters is time-consuming and may be impractical to compete in real time. In one of the conventional methods described above, a neighboring area of the film without holes therein is measured independently to find the value of the film thickness. This measured thickness value may be used subsequently in structure models for the film with holes therein to reduce the number of independent variables in the structure model. However, as is exemplified by wafer 12 in FIGS. 1A and 1B, there is no extra area of layer 12b without the presence of contact holes 13 therein for such separate measurement to be performed to determine the thickness h of layer 12b independently from the determination of the remaining parameters.

This invention is based on the recognition that, to simplify the structure model for measurement of the parameters related to the hole array, an approximate value of the thickness h of the layer 12b may be first found using a film model of the layer which does not vary the parameters related to the contact hole array. The thickness so found is more accurate where the diameter D of the holes 13 is less than one-third of the pitch P or spacing between the holes. The volume fraction occupied by the holes 13 is then slightly less than 0.1. In such event, a film model without varying the parameters (e.g. diameter, pitch, wall angle etc.) of the contact holes provides an estimate for the height h of sufficient accuracy for many applications. Another favorable condition for applying the above-described concept, using the film model, is that the reflectivity of the diffracted radiation from the array of holes 13 in layer 12b at certain wavelengths is less affected by parameters related to the diffracting structure, such as the hole diameter D. Before these issues are examined, it is first useful to describe the apparatus that may be used for measuring wafer 12 of FIGS. 1A and 1B.

Figure 2:
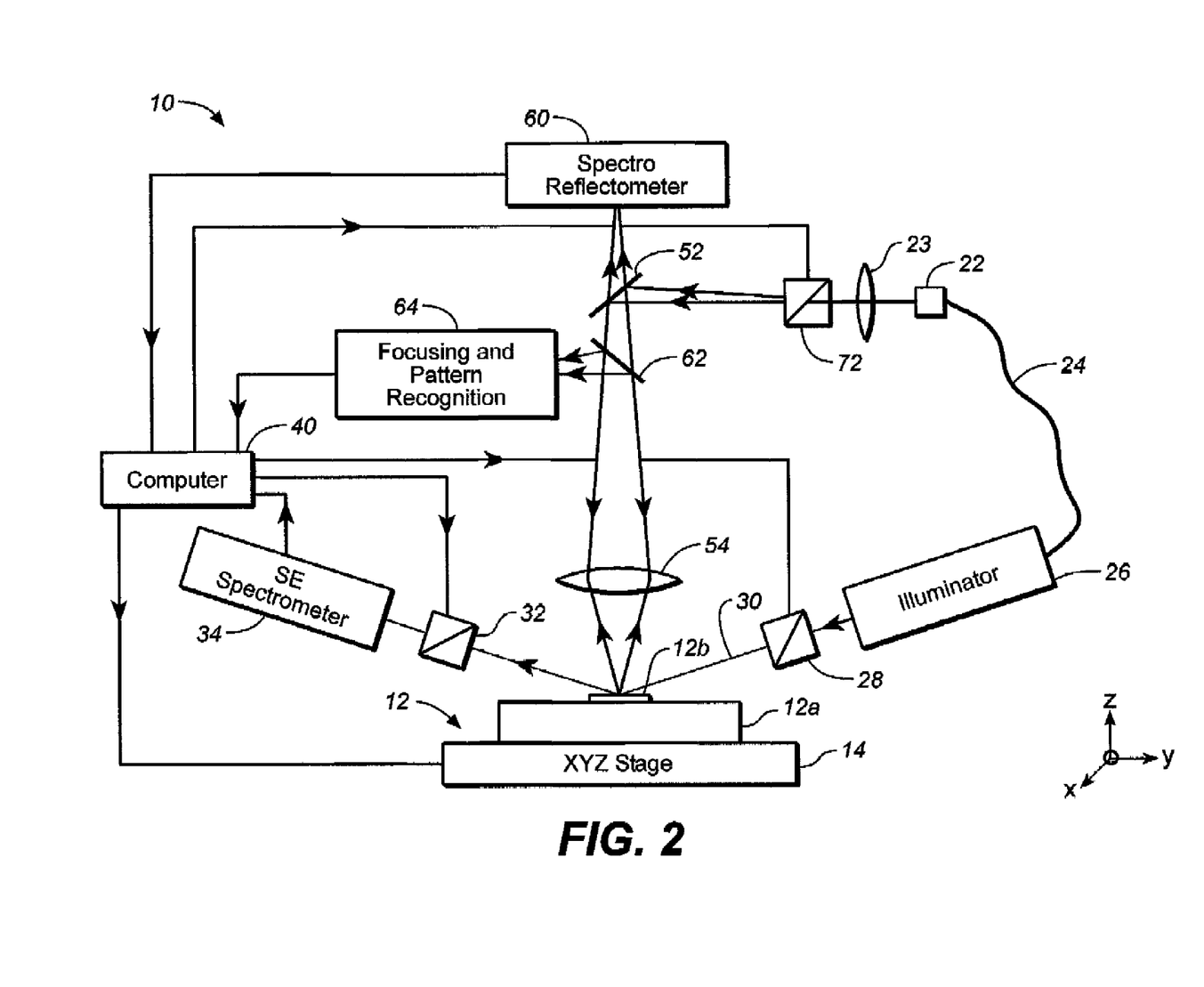
FIG. 2 is a schematic view of a spectroscopic scatterometer/reflectometer to illustrate an embodiment of the invention.

FIG. 2 is a schematic view of a spectroscopic scatterometer system 10 to illustrate the preferred embodiment of the invention. As shown in FIG. 2, system 10 advantageously combines features of a spectroscopic scatterometer, spectroscopic ellipsometer and spectroscopic reflectometer. The spectroscopic reflectometer or the spectroscopic ellipsometer may be used for measuring the film thickness of the layer containing the diffracting structure using a film model, and for subsequently measuring the spectra of the diffracted radiation from the array of contact holes 13 for determination of parameters related to the diffracting structure as explained below. As shown in FIG. 2, a semiconductor wafer 12 may comprise a silicon substrate 12a, a film 12b (such as a photoresist pattern) on the substrate having a two dimensional diffracting structure therein such as an array of contact holes in the film, where the film is at least partially light-transmissive and has a certain film thickness h and refractive index (n and k, the real and imaginary components of the index).

An XYZ stage 14 is used for moving the wafer in the horizontal XY directions in order to position the wafer relative to the optics. Stage 14 may also be used to adjust the z height of the wafer 12 as described below. In reference to FIG. 2, a broadband radiation source such as white light source 22 (or a source supplying radiation of a single or multiple wavelengths) supplies light through an optional fiber optic cable 24 which randomizes the polarization and creates a uniform light source for illuminating the wafer. Preferably, source 22 supplies electromagnetic radiation having wavelengths in the range of at least 230 to 800 nm. Upon emerging from fiber 24, the radiation passes through an optical illuminator that may include a slit aperture and a focus lens (not shown). The slit aperture causes the emerging light beam to image an area of layer 12b of dimensions that can be controlled. The light emerging from illuminator 26 is polarized by a polarizer 28 to produce a polarized sampling beam 30 illuminating the layer 12b, such as one with P- or S-polarization.

The radiation originating from sampling beam 30 that is reflected by layer 12b, passed through an analyzer 32 and to a spectrometer 34 to detect different spectral components of the reflected radiation. For a more detailed description of a spectroscopic ellipsometer, please see U.S. Pat. No. 5,608,526, issued Mar. 4, 1997, which is incorporated herein by reference in its entirety.

In the spectroscopic ellipsometry mode of system 10 for measuring film thickness, either the polarizer 28 or the analyzer 30 (or both) is rotated (to cause relative rotational motion between the polarizer and the analyzer) when spectrometer 34 is detecting the reflected light at a plurality of wavelengths, such as those in the spectrum of the radiation source 22, where the rotation is controlled by computer 40 in a manner known to those skilled in the art. The reflected intensities at different wavelengths detected is supplied to computer 40 which computes the film thickness and n and k values of the refractive index of layer 12b (or of a layer similar to layer 12b but without holes therein) in a manner described in more detail below. The film thickness and n and k values of the refractive index of a layer similar to layer 12b but without holes therein may be derived in a manner known to those skilled in the art, or as described in U.S. Pat. No. 5,608,526.

While spectroscopic ellipsometry may be preferred for measuring film thickness, in some applications a spectroscopic reflectometer (also known as spectroreflectometer and spectrophotometer) may be adequate for measuring the film thickness. For this purpose, lens 23 collects and directs radiation from source 22 to a beam splitter 52, which reflects part of the incoming beam towards the focus lens 54 which focuses the radiation to layer 12b. The light reflected by the layer 12b is collected by lens 54, passes through the beam splitter 52 to a spectrometer in the spectroscopic reflectometer 60. The spectral component(s) at a single or different wavelengths measured are detected and signals representing such components are supplied to computer 40 for determining the film thickness and refractive index in a manner described, for example, in U.S. Pat. No. 5,747,813. Spectroscopic devices other than the spectroscopic reflectometer and spectroscopic ellipsometer, or other devices may also be used for measuring the film thickness of layer 12b, such as polarimeters, and single wavelength ellipsometers or reflectometers, and are within the scope of the invention.

Other examples of such spectroscopic devices that may be used for determining the film thickness of layer 12b include the n & k Analyzer of n & k Technology Inc. of Santa Clara, Calif., and described in "Optical Characterization of Amorphous and Polycrystalline Silicon Films," by Ibok et al., reprinted from August 1995 edition of Solid State Technology published by PennWell Publishing Company; "Optical Dispersion Relations for Amorphous Semiconductors and Amorphous Dielectrics," by Forouhi et al., Physical Review B, vol. 34, no. 10, pp 7018-7026, Nov. 15, 1986; "Optical Properties of Crystalline Semiconductors and Dielectrics," by Forouhi et al., Physical Review B, vol. 38, no. 3, pp 1865-1874, Jul. 15, 1988 and U.S. Pat. No. 4,905,170.

For the purpose of adjusting the height of wafer 12 relative to the polarizer 28, analyzer 32 to achieve proper focus in the spectroscopic ellipsometry measurement, or relative to the focus lens 54 and spectroscopic reflectometer 60 in the spectroreflectometer measurement, the height of the wafer may need to be adjusted by means of stage 14 prior to the measurement. For this purpose, a portion of the radiation reflected by layer 12b and collected by lens 54 is reflected by a beamsplitter 62 towards a focusing and pattern recognition block 64 for comparing the reflected image to a pattern. Block 62 then sends information concerning the comparison to computer 40 which controls stage 14. Stage 14, in turn, moves the wafer 12 up or down in the vertical or Z direction in order to move wafer 12 to a proper height relative to the optical components of system 10.

The diffraction from the array of holes 13 may be measured using the apparatus or system 10 in FIG. 2 as described above. Once the film thickness of the film 12b has been obtained from the diffraction measured, a reference database may now be constructed by means of computer 40 using the film thickness value to simplify the structure model for layer 12b. The parameters pertaining to the diffracting structures may then be derived from the same data from which the film thickness is obtained (or alternatively, from diffraction data of the structures obtained in a separate measurement using the apparatus in FIG. 2). Instead of a reference database, a linear or non-linear optimization process can also be performed using the prior film thickness value so obtained as a fixed parameter, or as a seed value in a parameter estimation process where the film thickness is floated along with the parameters of the diffracting structure. As yet another alternative, a linear or non-linear optimization process can also be used in combination with a reference database.

Figure 3A:
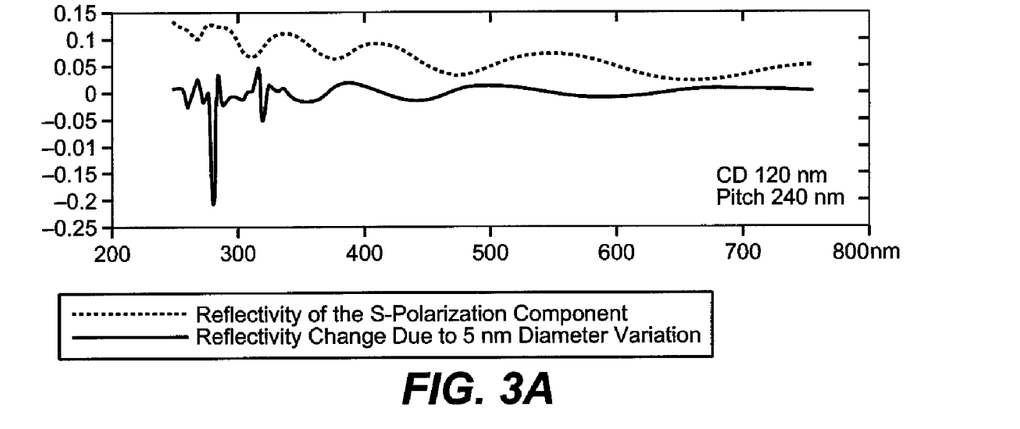
FIGS. 3A, 3B, and 3C are graphical plots of the reflectivities of the S-polarization components measured in three independent measurements of radiation that is scattered by three corresponding different layers measured independently of one another. Each layer has a two-dimensional array of contact holes therein, where the holes in the three layers have different diameters and are spaced at different pitches, useful for illustrating the invention. These graphical plots also show the changes in reflectivity of such components due to a 5 nanometer variation of contact hole diameters in the layers to illustrate the fact that the reflectivity spectrum is not sensitive to variations in hole diameter over the longer wavelengths portion of the spectrum.
Figure 3B:
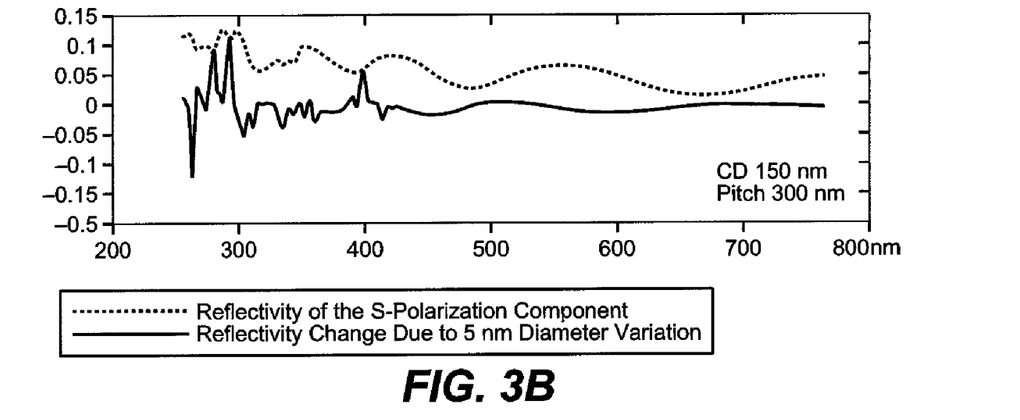
Figure 3C:
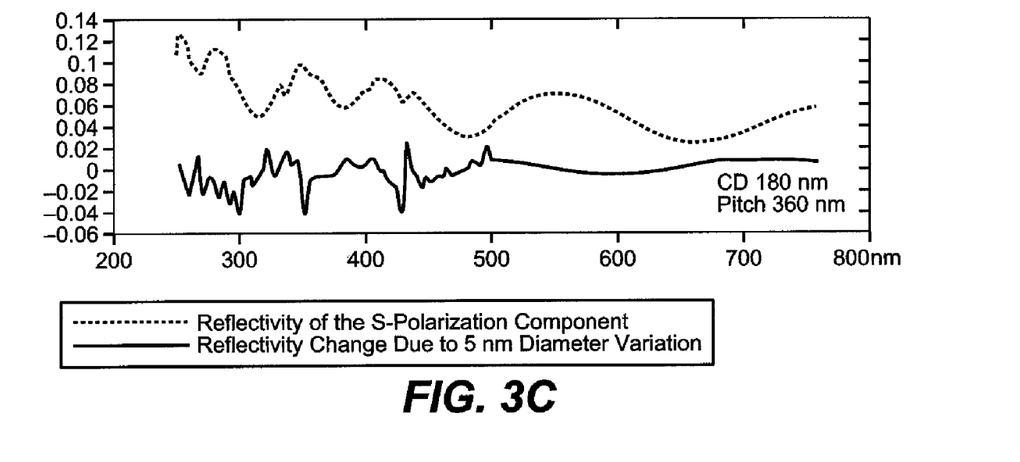

It is found that the reflectivity that is measured by system 10 does not change significantly within certain wavelength ranges as a result of changes in the hole diameter D. This is illustrated in FIGS. 3A-3C. As shown by the solid line in FIG. 3A, for example, where the hole diameter is of the order of 120 nanometers and the contact hole array has a pitch of 240 nanometers, the reflectivity measured by system 10 remains substantially the same when the hole diameter changes by up to 5 nanometers. In FIG. 3A, the dotted line curve is that of the reflectivity of S-polarization components and the solid-line curve is the change in reflectivity due to 5 nanometer hole diameter variation. As will be apparent from FIG. 3A, where the array of holes has a pitch of about 240 nm and hole diameter of about 120 nm, the reflectivity remains substantially constant, despite hole diameter variation of up to 5 nanometers, at wavelengths above 500 nanometers. FIGS. 3B and 3C illustrate the same phenomena with the hole diameter at around 150 nanometers and the pitch at about 300 nanometers (FIG. 3B), and the hole diameter at around 180 nanometers and pitch at about 360 nanometers (FIG. 3C). In each of FIGS. 3B and 3C, again, the dotted line curve represents the reflectivity of the S-polarization component and the solid-line curve represents the change in reflectivity due to 5 nanometer diameter variation. In FIGS. 3A-3C, the parameter CD, or critical dimension, is the diameter of the contact holes 13.

From the above, it is evident that it is possible to use a film model for obtaining an accurate estimate of the thickness or height of layer 12b where the film model does not parameterize and vary the hole diameter. This is especially true in the case where the film model is constructed only over a certain limited wavelength range, such as in the red and near infrared portion of the spectrum, or such as above about 500 nanometers as shown in FIGS. 3A-3C. It may be preferable to employ film models that have been modified to take into account effects of the presence of some diffracting structure(s) in or near the film, even though the parameters related to the structure(s) themselves are not varied in the model. Film models for calculating the thickness of films with diffracting gratings therein are known to those skilled in the art and will not be described in detail herein. For further details concerning such film models, please see "Effective-Medium Theory of Zeroth-Order Lamellar Gratings in Conical Mountings," by Charles W. Haggans et al., J. Opt. Soc. Am. A, Oct. 19, 1993, Volume 10, No. 10, Pages 2217-2225; "High-Order Effective-Medium Theory of Subwavelength Gratings in Classical Mounting: Application to Volume Holograms," by P. Lalanne et al., J. Opt. Soc. Am. A, Volume 15, No. 7, July 1998, Pages 1843-1851; "On the Effective Medium Theory of Subwavelength Periodic Structures," P. Lelanne, Journal of Modern Optics, 1996, Volume 43, No. 10, Pages 2063-2085; and "Effective Medium Theory of Two-Dimensional Subwavelength Gratings in the Non-Quasi-Static Limit," J. Opt. Soc. Am. A, Volume 15, No. 6, June 1998, Pages 1577-1585.

Using a film model, the thickness h of the layer 12b in FIGS. 1A and 1B can be found using a regression algorithm. Regression algorithms are known to those skilled in the art and will not be described here in detail. For an explanation of the regression method, please see "Spectroscopic Ellipsometry and Reflectometry: A User's Guide," by Harland G.

Tompkins and William A. McGahan, John Wiley & Sons, Inc., New York, 1999, Pages 101-107.

Figures 4A, 4B:
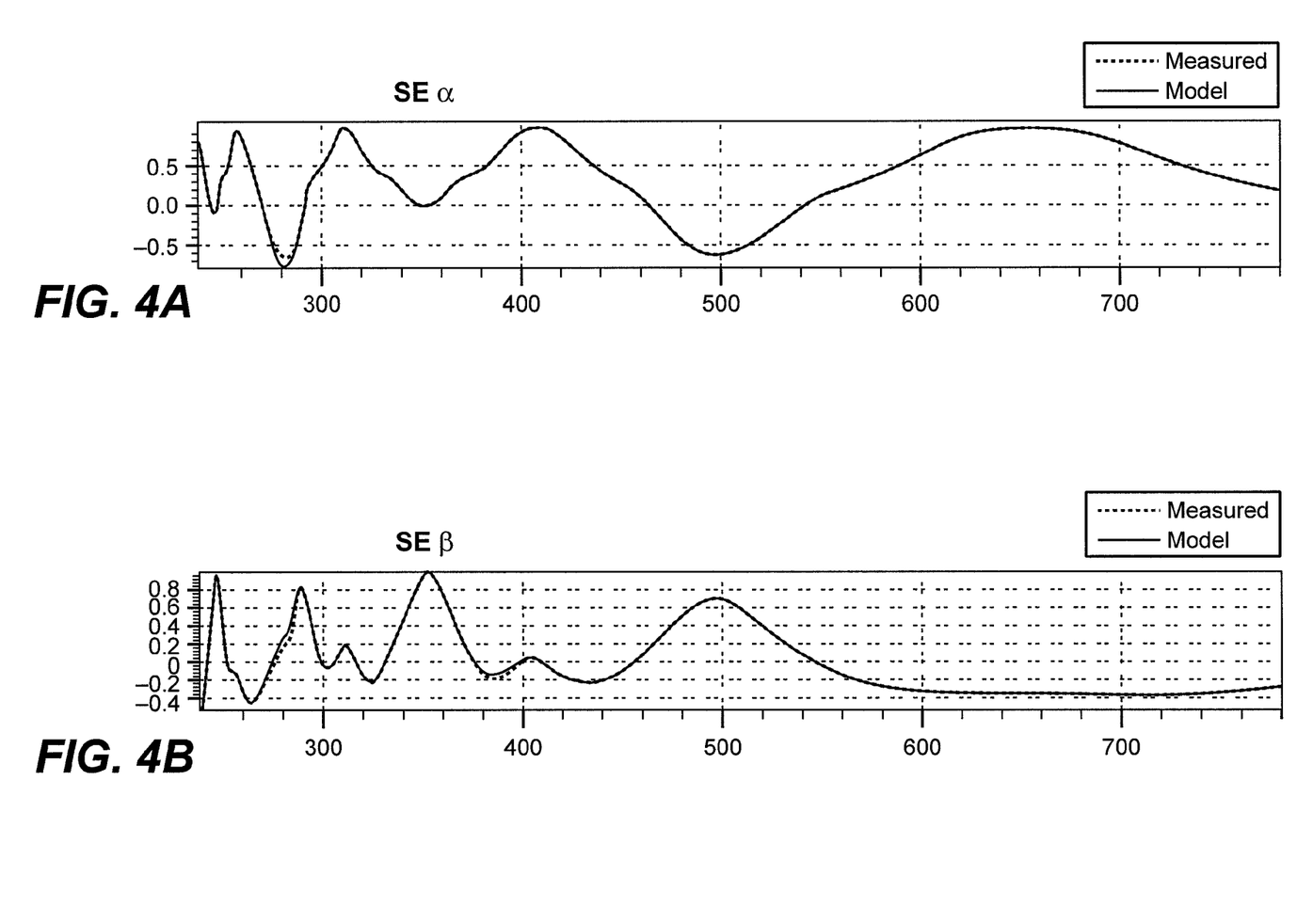
Figure 4C:
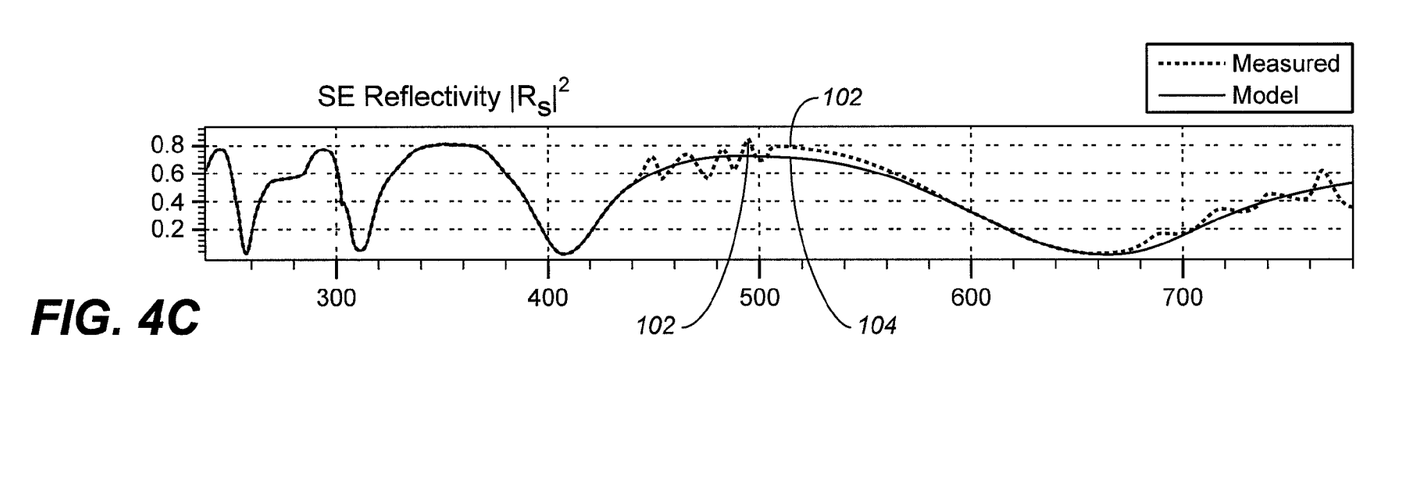
Figure 4D:
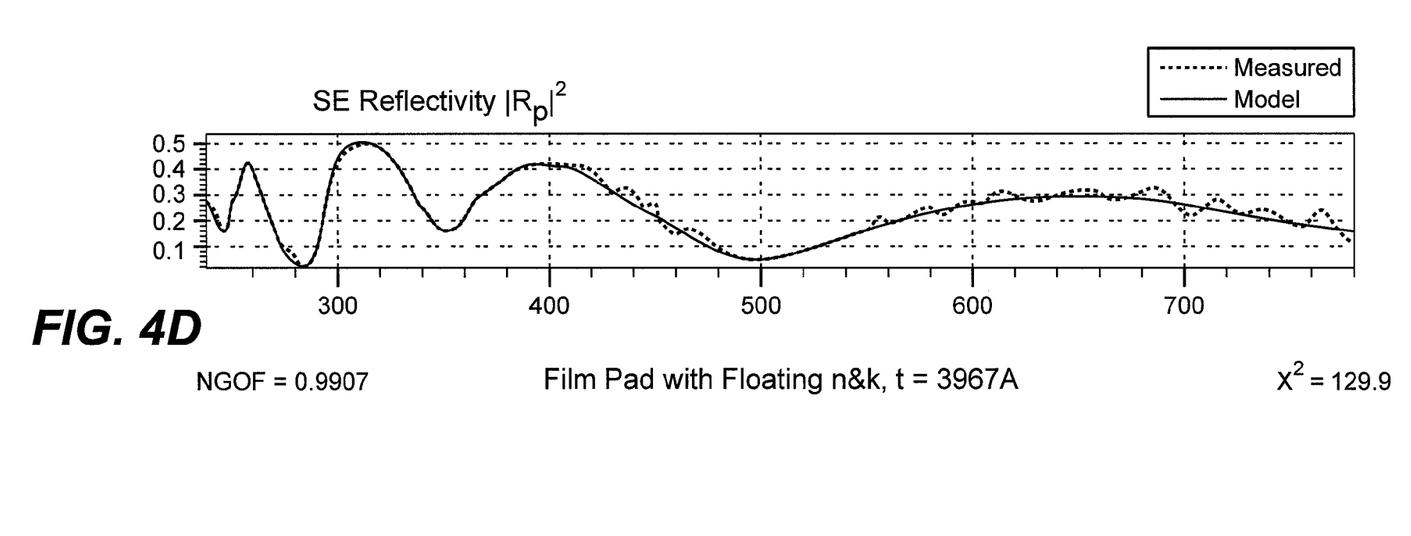
Figure 5A:
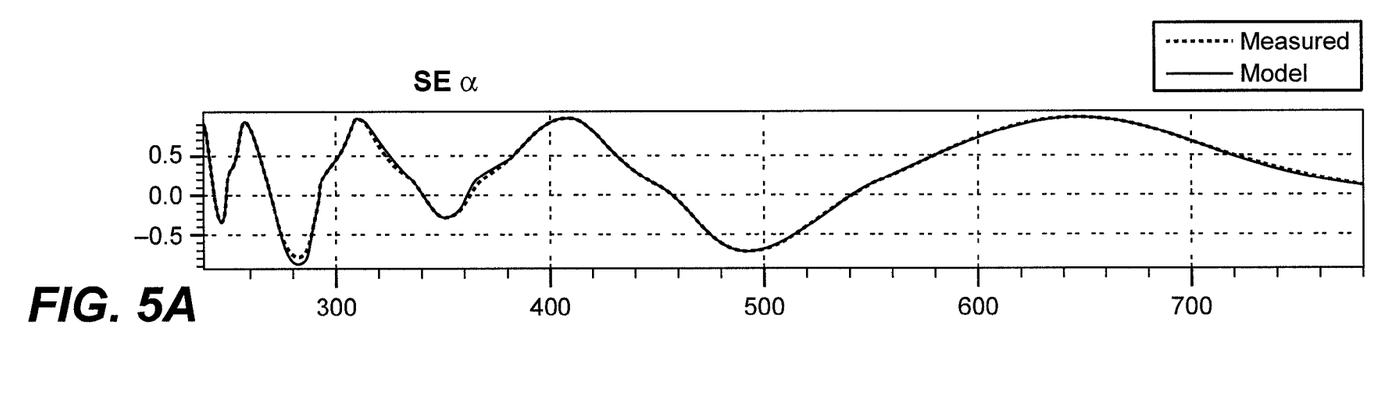
Figure 5B:
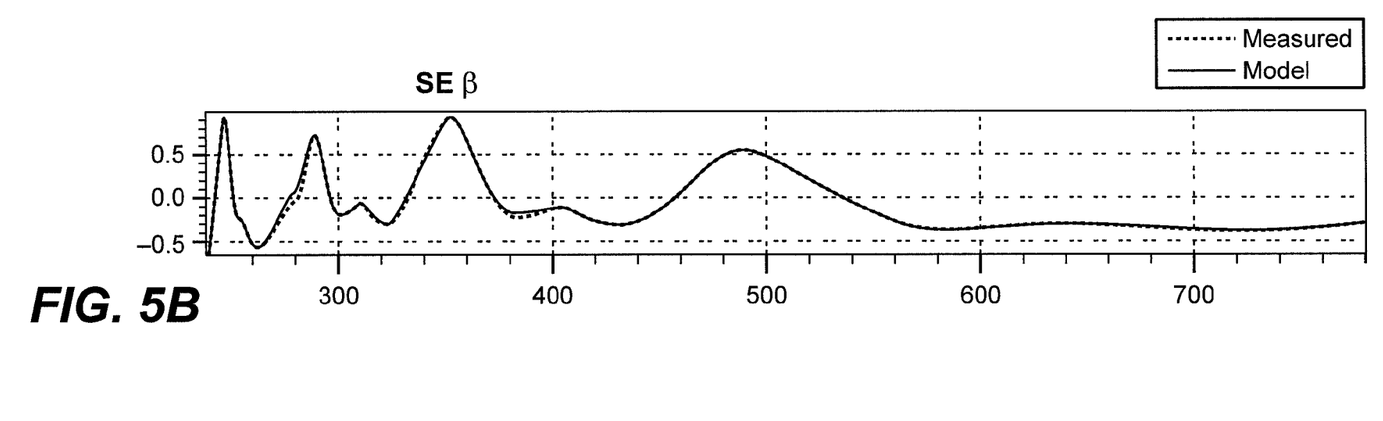
Figure 5C:
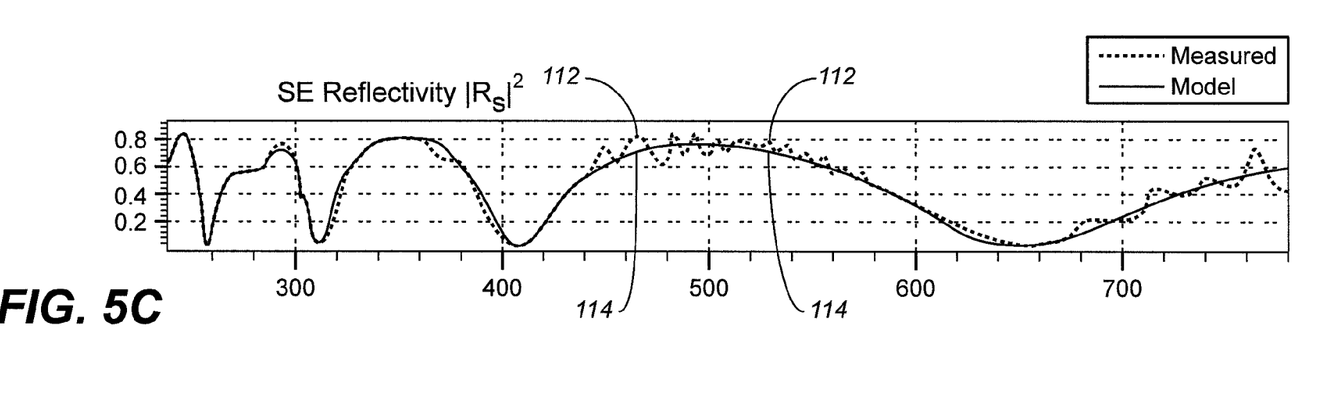
Figure 5D:
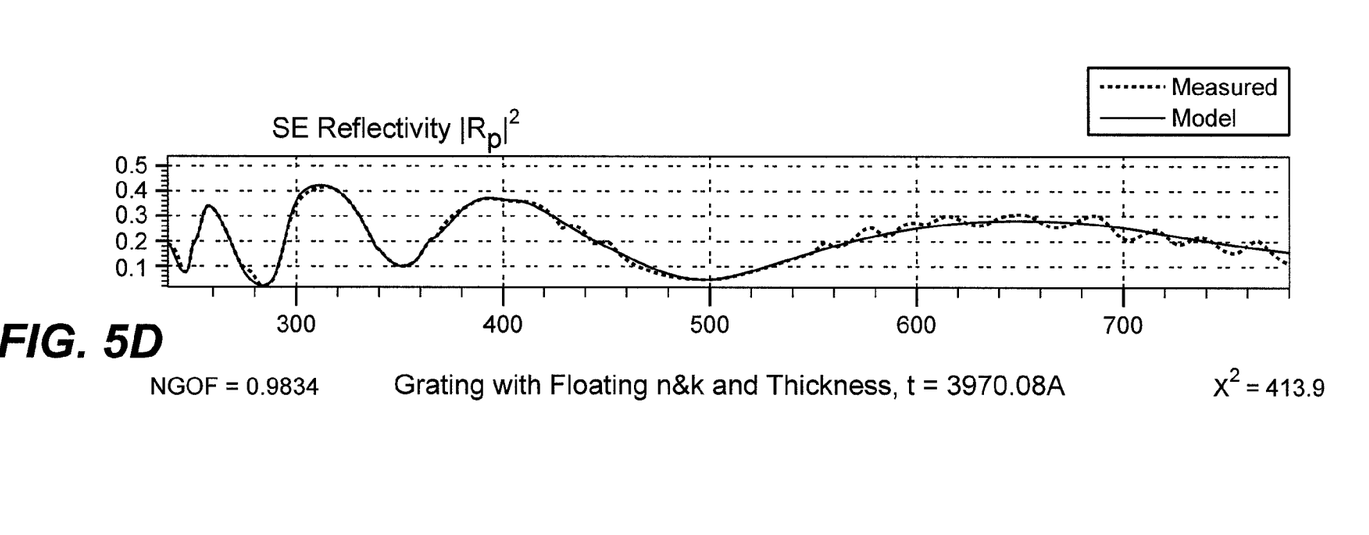
Figure 6A:
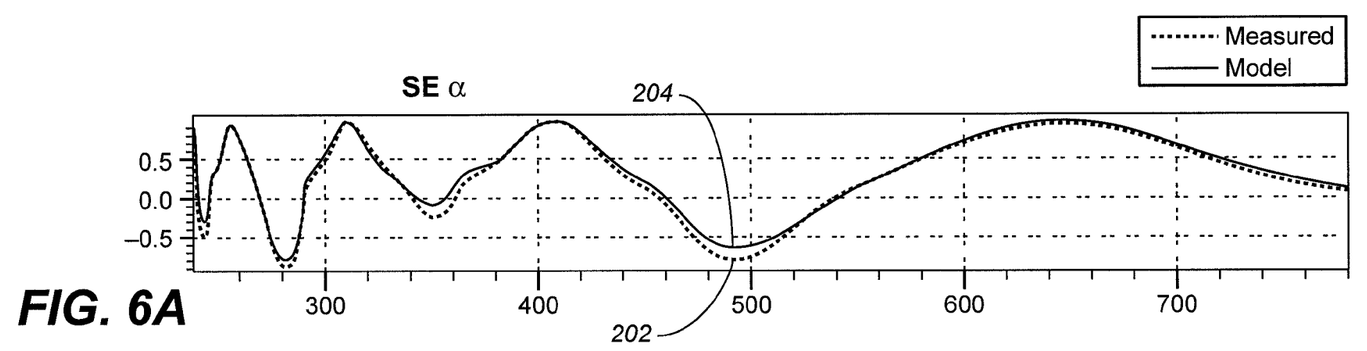
Figure 6B:
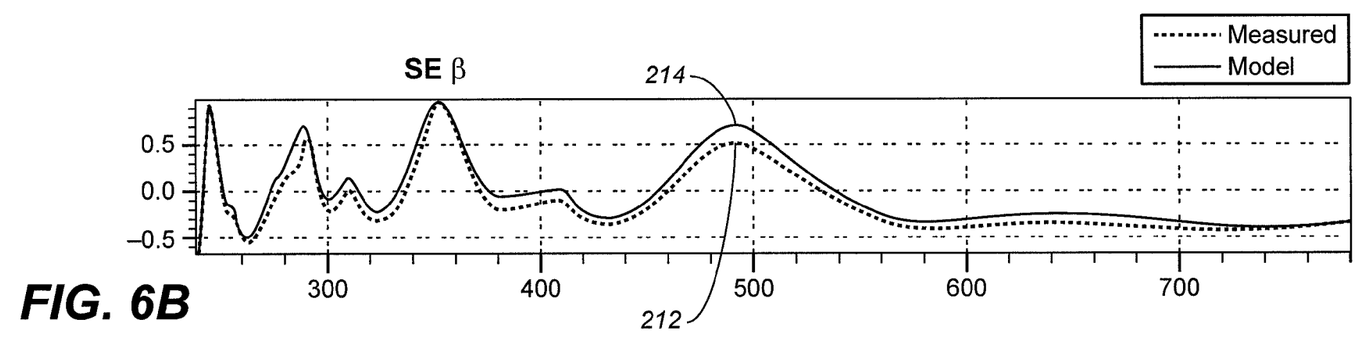
Figure 6C:
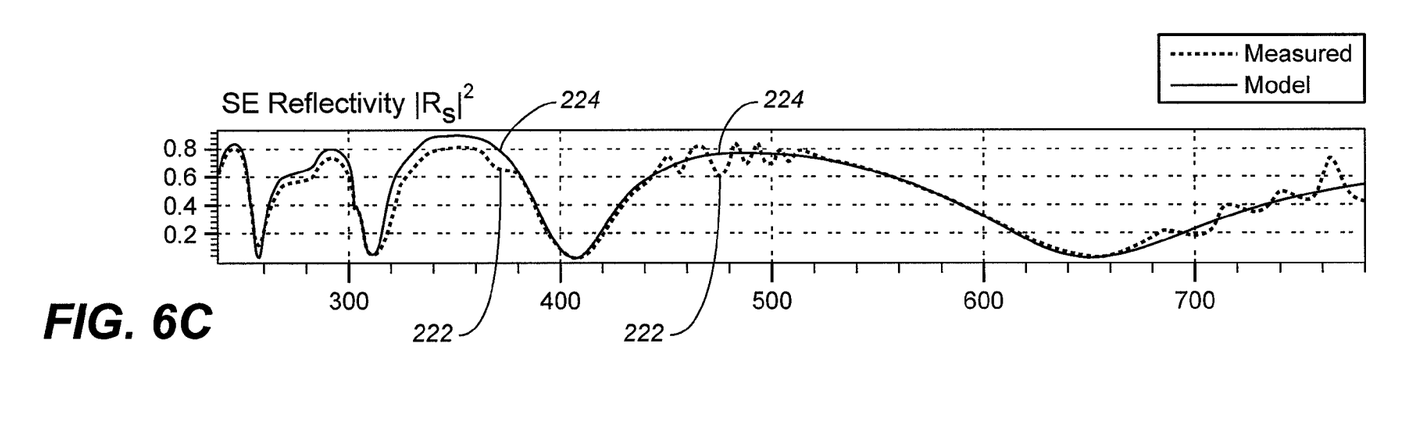
Figure 6D:
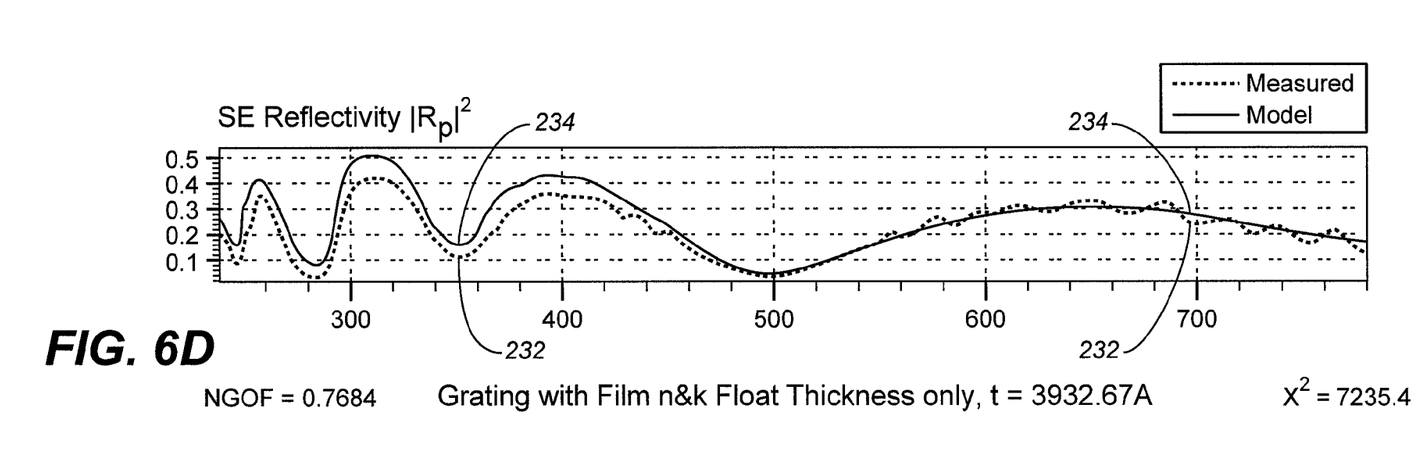

FIG. 4A is a graphical plot illustrating a comparison of the measured values and those calculated by a film model of the ellipsometric parameter α over a spectrum, when a layer similar to layer 12b but without contact holes therein is measured, to provide a reference value of the layer thickness. For an explanation of the ellipsometric parameters α and β, please see Bernoux et al., "Ellipsometrie," Techniques de l'Ingenieur, R6490, pp. 1-16 (1990). As shown in FIG. 4A, the measured values of α are shown in a light dotted line and those predicted by the model, are shown in a heavier dotted line. As shown in FIG. 4A, the measured values and those predicted by the model match and are substantially the same. The same appears to be true for the ellipsometric parameter of β and the reflectivity of the P-polarization component, as illustrated in FIGS. 4B and 4D. As for the reflectivity of the S-polarization components, the measured values 102 exhibit a small amount of oscillation between 450 and 500 nanometer wavelengths that do not appear in the predicted values and are slightly higher than those (104) predicted by the model in the range of 500 to 600 nanometers of wavelength. Aside from such deviation, the actual measured values of the ellipsometric parameters and reflectivities match substantially those predicted by the film model. In the results illustrated in FIGS. 4A-4B, the index of refraction variables n and k are varied in the film model, while also varying the thickness. The thickness arrived at by means of regression is 3967 angstroms.

FIGS. 5A-5D illustrate graphically a comparison of the measured values compared to those predicted by the modified film model of the ellipsometric parameters α and β, and the reflectivities of the S- and P-polarization components when layer 12b with contact holes therein is measured. In the results illustrated in FIGS. 5A-5D, the thickness of the layer 12b is also varied in the model, in addition to the effective index of refraction variables n and k. The parameters related to the contact holes such as diameter or hole profile, however, are not varied. As will be evident from a comparison between FIGS. 4A-4D on the one hand, and those of FIGS. 5A-5D on the other, the measured values and those predicted by the model in both sets of graphical plots are substantially the same. The measured values 112 in FIGS. 4C and 5C exhibit substantially the same behavior of oscillation between 400 to 500 nm, and are slightly higher than the predicted values 114 between 500 and 600 nm.

The thickness of layer 12b obtained by means of regression from the measurements and structure model illustrated in FIGS. 5A-5D is 3970.08 angstroms, which is close to the value 3967 angstroms obtained from measurement of the film pad without holes therein. This indeed demonstrates that the thickness obtained using a modified model of layer 12b that takes into account the presence of diffracting structures in the layer matches that obtained from measuring the film without contact holes therein. In the modified model, the index of refraction parameters n and k that are varied are the effective values for layer 12b with the contact holes 13 therein as seen by the system 10 in FIG. 2, and may be different from the index of refraction value of the material in layer 12b. As noted above, for improved accuracy, the regression process may be applied to the measured data and model in a limited range of wavelengths, such as data at only the red and near infrared wavelengths, or at and above 500 nm, or other wavelength ranges where the reflectivity is less affected by variations in the dimensions or profile of the diffracting structure.

FIGS. 6A-6D illustrate graphically a comparison of the measured values compared to those predicted by the modified film model of the ellipsometric parameters α and β, and the reflectivities of the S- and P-polarization components when layer 12b with contact holes therein is measured. In the results illustrated in FIGS. 6A-6D, the thickness of the layer 12b is varied in the model, but not the effective index of refraction variables n and k. As will be evident from a comparison between FIGS. 5A-5D on the one hand, and those of FIGS. 6A-6D on the other, varying only thickness without also varying the effective index of refraction variables n and k (FIGS. 6A-6D) yields results inferior to those where the effective index of refraction variables n and k are also varied (FIGS. 5A-5D). As shown in FIGS. 6A-6D, the measured values 202, 212, 222, 232 are close to but do match in a number of wavelength ranges the values 204, 214, 224, 234 predicted by the modified model. Thus, while varying only the thickness may be adequate for some applications, it is preferable to vary also the effective index of refraction variables n and k.

Figure 7:
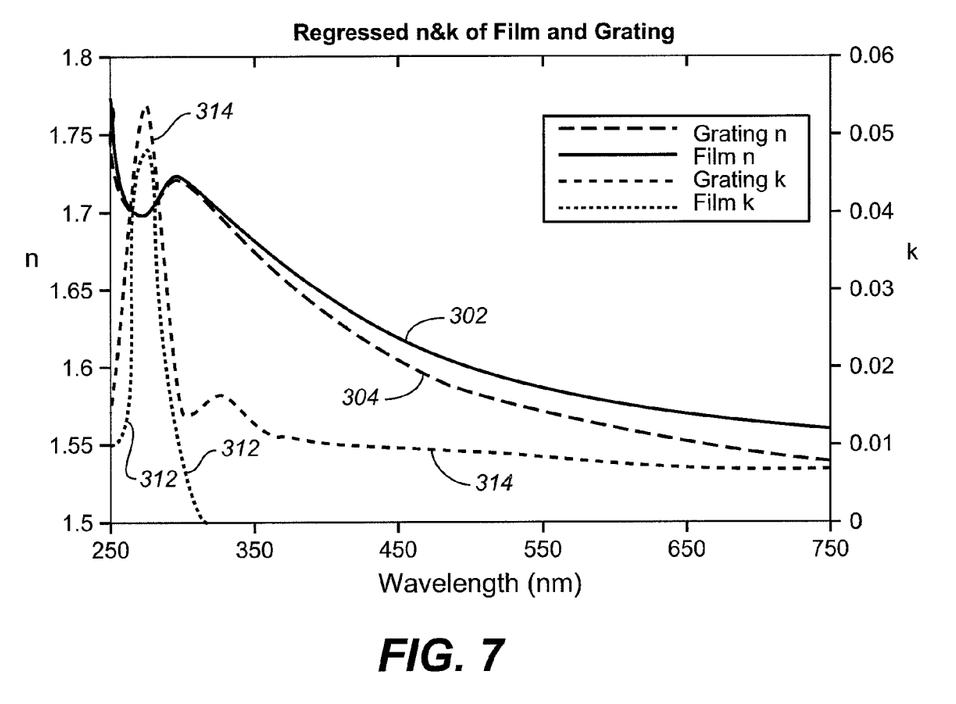
FIG. 7 is a graphical plot of the complex index of refraction n and k of a film pad without holes therein and that of a corresponding grating (film pad with a two-dimensional array of contact holes) to further illustrate the invention.

FIG. 7 is a graphical plot illustrating a comparison of the regressed values of n and k for a film similar to layer 12b but without holes therein and layer 12b. As shown in FIG. 7, the values 302 and 312 of n and k for the film without holes therein differ from the values 304 and 314 for the layer 12b with holes therein. The regression process for deriving layer thickness described above may also yield values for n and k. Hence, for some applications, the values for n and k obtained in the regression process described above for the film may differ significantly from those for layer 12b with holes therein so that they may not be helpful in further reducing the number of variables that need to be used subsequently in constructing a model for diffraction from the hole array. Nevertheless, it is observed that the regressed values for n for the film do not differ from those for the grating by large amounts, so that for some applications, it may be possible to use the regressed value of n obtained in the above process in obtaining the layer thickness to further reduce the number of model parameters that must be varied in modeling the diffraction from the contact hole array. Alternatively, when the thickness of the layer 12b is well established (for example in a stable manufacturing process), the values of index (n & k) derived using a film model incorporating effective medium theory may be used to generate the seed or starting values in a linear or non-linear optimization process for some of the profile parameters of the diffracting structure (e.g., hole diameter), thereby accelerating the convergence of this process.

After an estimate of the layer thickness (and optionally also the value of n) has been obtained as described above, a model with detected signal spectra of the diffraction from layer 12b with holes therein is then constructed in a manner described in more detail in U.S. Pat. No. 6,590,656, which is incorporated herein by reference in its entirety. In the embodiment where the same diffraction data is used for the separate and sequential derivation of both the film thickness and parameters pertaining to the diffracting structures, such parameters are then derived using the film thickness so obtained. In the alternative embodiment where parameters pertaining to the diffracting structures are obtained from data that are different from those used for thickness derivation, system 10 of FIG. 2 is then used to again measure the radiation diffracted from array of holes 13 in layer 12b, by directing an illumination beam to the layer, and detecting, preferably at a plurality of wavelengths the zeroth order diffraction from the layer in a manner described in more detail in U.S. Pat. No. 6,590,656, although detection at a single wavelength may be adequate for some applications. In both embodiments, a regression algorithm is then applied to the measured data and the model constructed which uses the estimated layer thickness (and optionally also the value of n) to find the values of parameters related to the diffracting structure, such as pitch, critical dimension (width of lines or diameter of holes), side wall angle or profile. The parameters that are varied by the regression algorithm include those related to the diffracting structure, and do not include the thickness of layer 12b. Where the values of the effective n and k (or only of k) are not known from the process for estimating layer thickness, n and k (or only k) may also be included as parameters that are varied in the process. Models for finding parameters related to the diffracting structure are described in U.S. patent applications "Parametric Profiling Using Optical Spectroscopic Systems," Ser. No. 09/741,663, filed Dec. 19, 2000, and "Improved System for Scatterometric Measurements and Applications," Ser. No. 09/671,715, filed Sep. 27, 2000, both of which are incorporated herein by reference in their entireties. The values of these parameters may be found using either the intensity or ellipsometric parameter data measured by system 10.

Figure 8:
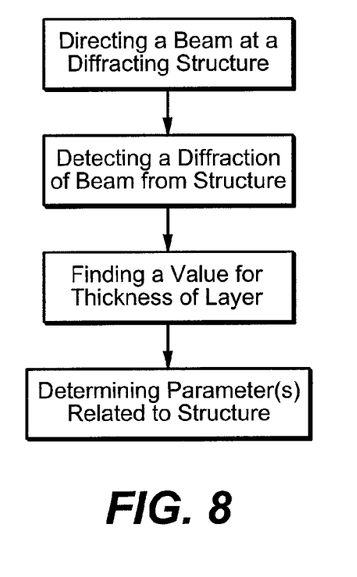
FIG. 8 is a flowchart illustrating a method for measuring a diffracting structure.

The two embodiments are illustrated in FIG. 8. As shown in FIG. 8, a beam of electromagnetic radiation of a plurality of wavelengths is directed at a sample with a layer containing a periodic diffracting structure. The diffraction of the beam at said plurality of wavelengths from said diffracting structure is detected. A value for thickness of the layer using a film model of the layer is found, either from the diffraction detected, or from data obtained in a separate measurement where the structure is illuminated by a beam and the diffraction of the beam by the structure is detected to obtain data. Then one or more parameters related to said diffracting structure is determined using the thickness value and the diffraction detected.

The information on film thickness obtained in the first step can be used to verify that the optical illumination and collection angles and aperture sizes are optimal for the measurement of the diffracting structure, prior to or during the grating profile parameter estimation process. For some multilayer film conditions, the most sensitive optical conditions for determining grating profile parameters can vary with film thickness. Based on the film thicknesses derived in the first parameter estimation step, and for measurement systems incorporating adjustable or selectable angles and aperture sizes, the optical illumination and collection angles and aperture sizes can be adjusted or selected to maximize the sensitivity of subsequent spectroscopic and angular measurement data, either for the same site as the first step, or the next site on the same wafer, or on the next wafer.

While the invention has been described above by reference to various embodiments, it will be understood that changes and modifications may be made without departing from the scope of the invention, which is to be defined only by the appended claims and their equivalents. For example, while the embodiments have been described for measuring the parameters related to a two-dimensional array of holes, the same embodiments may be used to measure parameters related to other diffracting structures, such as a two-dimensional array of pillars, grating lines or a one-dimensional array of holes. All references referred to herein are incorporated by reference in their entireties.

What is claimed is:

1. A method for measuring a sample with a layer containing a periodic diffracting structure, said method comprising:
   directing a first beam of electromagnetic radiation of a plurality of wavelengths at said periodic diffracting structure;
   detecting a diffraction of said first beam at said plurality of wavelengths from said diffracting structure;
   finding a value for thickness of the layer using a film model of the layer, wherein said finding employs a film model that employs data restricted to those within a range of selected wavelengths or at selected wavelengths, at which reflectivity of the periodic diffracting structure is less sensitive to changes in dimensions or profile of the structure than to such changes at wavelengths that are outside such range or at wavelengths that are different from the selected wavelengths; and
   determining one or more parameters related to said diffracting structure using said thickness value and the diffraction detected.

2. The method of claim 1, wherein said finding employs a reflectometer or a ellipsometer.

3. The method of claim 1, wherein said finding employs a spectroscopic reflectometer or a spectroscopic ellipsometer.

4. The method of claim 1, wherein said finding employs a film model that employs data restricted to those of wavelengths within red and near infrared ranges.

5. The method of claim 1, wherein said finding includes:
   directing a second beam of electromagnetic radiation of a plurality of wavelengths at a section of said layer that includes at least a portion of said periodic diffracting structure; and
   detecting intensity or ellipsometric data of the second beam after it has been modified by the section of said layer.

6. The method of claim 5, wherein said finding employs a film model that uses parameters including thickness and indices of refraction of the layer, but no parameter related to dimensions or profile of the diffracting structure.

7. The method of claim 6, wherein said finding varies values of parameters related to indices of refraction of the layer.

8. The method of claim 1, wherein said finding finds the thickness value from the diffraction detected.

9. The method of claim 8, wherein said finding employs a film model that uses parameters including thickness and indices of refraction of the layer, but no parameter related to dimensions or profile of the diffracting structure.

10. The method of claim 9, wherein said finding varies values of parameters related to indices of refraction of the layer.

11. The method of claim 1, wherein said finding employs a film model that uses parameters including thickness and indices of refraction of the layer, but no parameter related to dimensions or profile of the diffracting structure.

12. The method of claim 1, wherein said finding varies values of parameters related to indices of refraction of the layer.

13. The method of claim 1, wherein said finding finds the value for thickness by measuring a section of the layer that includes at least a portion of the structure from which said diffraction is detected.

14. The method of claim 1, wherein said determining includes applying a regression algorithm that uses the thickness value.

15. The method of claim 1, wherein said determining includes applying a regression algorithm that determines the one or more parameters related to said diffracting structure.

16. The method of claim 15, wherein said regression algorithm varies values of only parameters pertaining to dimensions or profile of the diffracting structure, or both, and wherein said parameters that are varied do not include thickness of the layer.

17. The method of claim 16, wherein said parameters that are varied pertain to width or diameter and side wall angle of the structure.

18. The method of claim 1, wherein said detecting detects intensity or ellipsometric data from the diffraction, and said determining determines the one or more parameters related to said diffracting structure using the detected intensity or ellipsometric data.

19. The method of claim 1, wherein said determining comprises constructing a reference database using the thickness value.

20. The method of claim 1, said determining further comprising a linear or non-linear optimization process that uses the thickness value as a fixed parameter.

21. The method of claim 1, said determining comprising a linear or non-linear optimization process that uses the thickness value as seed value in a parameter estimation process where the thickness value is floated along with the parameters of the diffracting structure.

22. The method of claim 1, wherein said finding also finds the value(s) of the refractive index of the layer using a film model.

23. The method of claim 22, said determining comprising using the value(s) of the refractive index of the layer to generate seed or starting values in a linear or non-linear optimization process for some of the parameters of the diffracting structure, thereby accelerating the convergence of the process.

24. The method of claim 1, said method further comprising adjusting or selecting one or more of the following: an optical illumination angle, aperture size(s) of the first beam and collection angle for the detecting, in response to the thickness value, to maximize sensitivity of data to variations in parameters of the diffracting structure.

25. The method of claim 24, wherein the finding precedes the directing and detecting and finds the thickness value of a section of said layer that includes at least a portion of said periodic diffracting structure, and wherein said directing directs and said detecting detects from said section or a different section of said layer that includes at least a portion of said periodic diffracting structure.

26. The method of claim 24, wherein the finding precedes the directing and detecting and finds the thickness value of a section of said layer that includes at least a portion of said periodic diffracting structure, and wherein said directing directs the first beam to, and said detecting detects front, a section of a layer that includes a periodic diffracting structure different from the one from which the thickness value is found.

27. A method for measuring a sample with a layer containing a periodic diffracting structure, said method comprising:
    directing a first beam of electromagnetic radiation of a plurality of wavelengths at said periodic diffracting structure;
    detecting a diffraction of said first beam at said plurality of wavelengths from said diffracting structure;
    finding a value for thickness of the layer using a film model of the layer and the diffraction detected, wherein said finding employs a film model that uses parameters including thickness and indices of refraction of the layer, but no parameter related to dimensions or profile of the diffracting structure; and
    determining one or more parameters related to said diffracting structure using said thickness value and the diffraction detected.

28. The method of claim 27, wherein said determining includes applying a regression algorithm that uses the thickness value.

29. The method of claim 27, wherein said determining includes applying a regression algorithm that determines the one or more parameters related to said diffracting structure.

30. The method of claim 29, wherein said regression algorithm varies values of only parameters pertaining to dimensions or profile of the diffracting structure, or both, and wherein said parameters that are varied do not include thickness of the layer.

31. The method of claim 30, wherein said parameters that are varied pertain to width or diameter and side wall angle of the structure.

32. The method of claim 27, wherein said finding also finds the value(s) of the refractive index of the layer using a film model.

33. The method of claim 32, said determining comprising using the value(s) of the refractive index of the layer to generate seed or starting values in a linear or non-linear optimization process for some of the parameters of the diffracting structure, thereby accelerating the convergence of the process.

34. The method of claim 27, said method further comprising adjusting or selecting one or more of the following: an optical illumination angle, aperture size(s) of the first beam and collection angle for the detecting, in response to the thickness value, to maximize sensitivity of data to variations in parameters of the diffracting structure.

35. The method of claim 34, wherein the finding precedes the directing and detecting and finds the thickness value of a section of said layer that includes at least a portion of said periodic diffracting structure, and wherein said directing directs and said detecting detects from said section or a different section of said layer that includes at least a portion of said periodic diffracting structure.

* * * * *